(12) United States Patent
Marsh et al.

(10) Patent No.: US 8,728,085 B2
(45) Date of Patent: May 20, 2014

(54) BONE CUTTING ASSEMBLY

(75) Inventors: Andrew Marsh, London (GB); Uri Verthime, London (GB)

(73) Assignee: Depuy International Limited (GB)

( * ) Notice: Subject to any disclaimer, the term of this patent is extended or adjusted under 35 U.S.C. 154(b) by 220 days.

(21) Appl. No.: 13/322,725

(22) PCT Filed: Apr. 29, 2010

(86) PCT No.: PCT/GB2010/050701
§ 371 (c)(1),
(2), (4) Date: Feb. 10, 2012

(87) PCT Pub. No.: WO2010/136784
PCT Pub. Date: Dec. 2, 2010

(65) Prior Publication Data
US 2012/0130378 A1    May 24, 2012

(30) Foreign Application Priority Data
May 28, 2009   (GB) .................................. 0909121.6

(51) Int. Cl.
A61B 17/56   (2006.01)
A61B 17/14   (2006.01)
A61B 17/15   (2006.01)
A61B 17/16   (2006.01)
A61B 17/17   (2006.01)

(52) U.S. Cl.
USPC ................... 606/87; 606/80; 606/82; 606/88; 606/96

(58) Field of Classification Search
USPC ................... 60/79–90, 96–98, 102, 104, 105; 606/79–90, 96–98, 102, 104, 105
See application file for complete search history.

(56) References Cited

U.S. PATENT DOCUMENTS 5,031,203 A * 7/1991 Trecha ......................... 378/205
5,426,687 A * 6/1995 Goodall et al. ............... 378/206
5,569,260 A   10/1996 Petersen
5,661,775 A   8/1997 Cramer (Continued)

FOREIGN PATENT DOCUMENTS

DE   20008871 U1   8/2000
FR   2917284 A1    12/2008

OTHER PUBLICATIONS

PCT International Search Report PCT/GB2010/050701 dated Aug. 5, 2010.
GB Search Report GB0909121.6 date of search Sep. 24, 2009.

*Primary Examiner* — Michael T Schaper

(57) ABSTRACT

An assembly for use in cutting a bone during a surgical procedure comprises a cutting tool and a guide block. The cutting tool includes a blade and a drive unit for imparting a cutting motion to the blade. The guide block can be positioned against the bone and has a reference surface for guiding the blade during the cutting step, the guide block having a screen surface which provides a point of reference to indicate proper alignment of the blade. The cutting tool includes means for directing a collimated beam of light in a direction parallel to the blade, on to the screen surface on the guide block when the blade is in contact with the guide surface, the distance between the blade axis and the light beam being equal to the distance between the reference surface and the point of reference on the screen surface.

8 Claims, 3 Drawing Sheets

(56) References Cited

U.S. PATENT DOCUMENTS

| | | | |
|---|---|---|---|
| 6,565,227 B1 * | 5/2003 | Davis | 362/119 |
| 6,692,200 B2 * | 2/2004 | Peterson | 408/1 R |
| 6,743,235 B2 * | 6/2004 | Subba Rao | 606/91 |
| 7,200,516 B1 * | 4/2007 | Cowley | 702/151 |
| 7,331,113 B1 * | 2/2008 | Patrick et al. | 33/286 |
| 7,510,557 B1 * | 3/2009 | Bonutti | 606/86 R |
| 7,670,342 B2 * | 3/2010 | Bharadwaj et al. | 606/79 |
| 2002/0164217 A1 * | 11/2002 | Peterson | 408/1 R |
| 2003/0028196 A1 | 2/2003 | Bonutti | |
| 2005/0232713 A1 * | 10/2005 | Turner et al. | 408/16 |
| 2006/0159536 A1 * | 7/2006 | Pu | 408/241 G |
| 2007/0030486 A1 * | 2/2007 | Gelbart | 356/399 |
| 2007/0043375 A1 * | 2/2007 | Anissian | 606/87 |
| 2007/0219559 A1 * | 9/2007 | Heavener et al. | 606/87 |
| 2008/0269757 A1 * | 10/2008 | McMinn | 606/87 |
| 2009/0030417 A1 * | 1/2009 | Takahashi | 606/96 |
| 2010/0198275 A1 * | 8/2010 | Chana et al. | 606/86 R |
| 2012/0308322 A1 * | 12/2012 | Iannotti et al. | 408/115 R |

* cited by examiner

BONE CUTTING ASSEMBLY

CROSS REFERENCE TO RELATED APPLICATION

This application is a National Stage 35 U.S.C. 371 of International Patent Application PCT/GB2010/050701 filed Apr. 29, 2010.

BACKGROUND OF THE INVENTION

This invention relates to an assembly for use in cutting a bone during a surgical procedure.

The outcome of an orthopaedic surgery procedure, such as a procedure to replace an orthopaedic joint prosthesis, depends on the accuracy with which the bone is prepared. Bone preparation frequently involves cutting the bone, for example using a tool such as a saw or a drill or a burr cutting tool. Accuracy requires that the cut should be located accurately and oriented accurately.

It is common to use a cutting guide to locate a cut accurately. A cutting guide can be fastened to a bone in a step to prepare the bone for the subsequent cutting step, for example by means of pins. The cutting guide provides a guide surface which can support the blade of a cutting tool during the cutting step. For example, when the cutting tool is a saw with a reciprocating blade, the guide surface will usually be planar, for example in the form of an exposed planar surface or a slot. When the cutting tool is a drill or a burr cutter with a rotating bit, the guide surface can be a bore.

It is desirable to minimise inaccuracies which result from application of a force to the cutting tool which has a component which is not parallel to the axis of the blade. Such forces can tilt a blade introducing inaccuracy into the location or orientation or both of the blade, especially when the blade is not a tight fit in a guide slot or bore. Such forces might also tend to bend the blade.

BRIEF SUMMARY OF THE INVENTION

The present invention provides an assembly in which a beam of light is directed from the cutting tool in a direction parallel to the cutting blade on to a screen surface on a cutting guide, the surface providing a point of reference to indicate proper alignment of the blade.

Accordingly, in one aspect, the invention provides an assembly for use in cutting a bone during a surgical procedure, which comprises:
  a. a cutting tool which includes a blade and a drive unit for imparting a cutting motion to the blade, and
  b. a guide block which can be positioned against the bone and which has a reference surface for guiding the blade during the cutting step, the guide block having a screen surface which provides a point of reference to indicate proper alignment of the blade,
in which the cutting tool includes means for directing a collimated beam of light in a direction parallel to the blade, on to the screen surface on the guide block when the blade is in contact with the guide surface, the distance between the blade axis and the light beam being equal to the distance between the reference surface and the point of reference on the screen surface.

The assembly of the invention provides a surgeon with a visible indication that a force is applied to a cutting blade having a component in a direction which is perpendicular to the axis of the blade. The indication that a force is applied to the blade, having a component in a direction which is perpendicular to the blade's axis, is apparent through the relative positions of the point of incidence of the light beam on the screen and the reference mark. Such forces might tend to cause the blade to bear preferentially against one or more edges of the reference surface or to bend the blade or both. Such applied forces can introduce inaccuracy into the location or the orientation or both of the cut which is created by the blade, especially when the reference surface is open (rather than being closed in the form of a slot or bore) or the blade is a loose fit in a slot or bore. The bending forces can cause additional friction between the blade and the reference surface, possibly leading to wear of the blade or the reference surface or each of them and generation of undesirable wear debris. Vibration can lead to undesirable movement of the guide block on pins or other components which are used to fix it to the bone, or to loosening of such pins.

The invention uses a reference surface on a cutting guide to locate the blade of a cutting tool. The light source, with the reference surface, provides information concerning alignment of the blade when positioned in relation to the reference surface.

The point of reference can be a reference mark on the screen surface, for example in the form of an indented or raised profile on the surface, or a mark which is printed on the screen surface in a colour which contrasts with that of the surrounding surface, or a combination of an indented or raised profile and a printed mark.

The point of reference can be provided by an edge of the screen.

The reference surface on the guide block can be generally planar, for example provided by an exposed surface of the block or by a slot. It can be used to guide a saw blade or the rotating bit of a burr cutter. The point of reference can be in the form of a line which extends parallel to the reference surface. Preferably, the line is continuous. However, it might be discontinuous, for example provided by a line of dots or dashes. The line which provides the point of reference can be defined by an edge of the screen.

The reference surface can be provided by a bore. It can be used to guide a bore forming tool such as the rotating bit of a drill, which can slide in the bore. The reference mark can mark a point which is located a pre-determined distance from the bore in the guide block.

The assembly can include a light source which provides the source of the beam of light. The light source can be mounted on the cutting tool so that it is or forms part of the means for directing the beam of light. The light source might be a laser. The selection of the laser source should be made taking account of the visibility of the emitted light. It can be preferred for some applications for the laser source to emit light which is coloured green. Other factors which should be taken into account include supply of power, the generation of heat, and other safety issues. Suitable light sources are commercially available.

The assembly can include a fibre optic light conduit for conveying light from a source to the cutting tool. The fibre optic light conduit can have a free end from which the collimated beam of light is directed and which is fastened at the said end to the cutting tool so that it is or forms part of the means for directing the beam of light. The fibre optic light conduit has the advantage that a light source can be located remote from the cutting tool, so that the tool can be less bulky and it is not necessary to supply power for the light source to the cutting tool. The fibre optic light conduit and the light source might both be provided on the cutting tool so that the two components are or form part of the means for directing the beam of light. The assembly can include a light source which is remote from the cutting tool, which is connected to the cutting tool by means of the fibre optic light conduit.

The means for directing the collimated beam of light should be fastened to the cutting tool so that the beam is directed parallel to the axis of the blade when the blade is in use. When the blade is a saw blade, it might be made to reciprocate side-to-side in a plane by the drive unit. The beam of light should be directed parallel to that plane. The source of the light beam can reciprocate with the blade. Preferably however the beam of light is fixed as the blade reciprocates, for example to the drive body which imparts the reciprocating motion to the blade. When the blade is a bit (for example a drill bit or the bit of a burr cutter) which rotates about an axis, the beam of light should be directed parallel to the axis. The means for directing the light beam should be fastened to the cutting tool sufficiently rigidly that it does not move when the cutting tool is in use, for example by means of clamps. For example, a clamp might encircle the cutting tool body or might be screwed into the cutting tool body.

Preferably, the screen surface is provided by a screen which can be mounted detachably on the guide block. A detachable screen surface can be removed from the guide block after the cutting step. This has the advantage of reducing obstructions to viewing the surgery site. The screen surface should be fastened to the guide block sufficiently rigidly to prevent it from moving significantly during the cutting step. It can be fastened to the guide block by means of fasteners such as screws. However, it is preferred that it can be fastened to the guide block by means of resilient clips which facilitate attachment and subsequent removal.

The screen surface can be provided by a surface of the cutting guide which is formed as one piece with the cutting guide, or formed as separately from the cutting guide but fastened to the guide so that it would not be expected to be separated from the guide during use.

When the screen surface is provided by a screen which can be detached from the cutting guide, it can be formed from a material which is different from that of the cutting guide. The screen might be made from a polymeric material or from a metal. The use of a polymeric material can be preferred for ease of manufacture and cost, especially if the screen includes features which can be deformed resiliently to aid fixation to the cutting guide.

The cutting guide can be made from materials which are conventionally used in the manufacture of surgical instruments. Examples of suitable materials include metals such as stainless steels and polymeric materials. It can be preferred for some applications that at least the reference surface is provided by a metal because of its resistance to damage as a result of abrasion.

The reference mark should be such that it can be observed clearly during the surgical procedure. It might be provided as a profile feature, for example raised or indented, which can be moulded or machined. It might be provided by a marking having a contrasting colour, for example by printing. The reference mark might be provided by a combination of a profile feature and a contrasting colour.

The reference mark should be provided so that it is readily visible to a surgeon who is using the assembly. For example, it will generally be appropriate for the reference mark to have a transverse dimension of at least about 0.5 mm.

The light beam should be readily visible to a surgeon who is using the assembly. The visibility of the beam will depend on the frequency of the light in the beam, its intensity, and the size of the beam. Preferably, the transverse dimension of the beam is at least about 0.5 mm. The wavelength of the light should be such that it is visible against the screen, through its colour contrasting with that of the screen.

The reference surface in the cutting guide can be provided by an opening such as a slot or a bore. The blade (which might be a saw blade or a rotating bit of a drill or burr cutting tool) should be a sliding fit in the opening, as is known.

The reference surface can be provided by an exposed surface of the cutting guide.

The cutting guide should be fixed relative to the bone before the cutting step. The cutting guide can have bores formed in it for receiving fasteners such as pins or screws. The cutting guide can be fastened to other components of a surgical instrument set which can locate the cutting guide as required, such as for example an extramedullary rod. The cutting guide can be positioned relative to the bone using conventional techniques including references to anatomical landmarks using alignment instruments, and image guided surgery techniques.

The assembly of the invention can be used to position a tibial cutting guide relative to the tibia in a procedure to implant the tibial component of a knee joint prosthesis. It can be used to position a cutting guide relative to other bones in other procedures, for example in procedures to implant components of other orthopaedic joints such as the hip, ankle, shoulder and elbow.

BRIEF DESCRIPTION OF THE DRAWINGS

Embodiments of the invention are described below by way of example with reference to the accompanying drawings, in which.

DETAILED DESCRIPTION OF THE INVENTION

Figure 1:
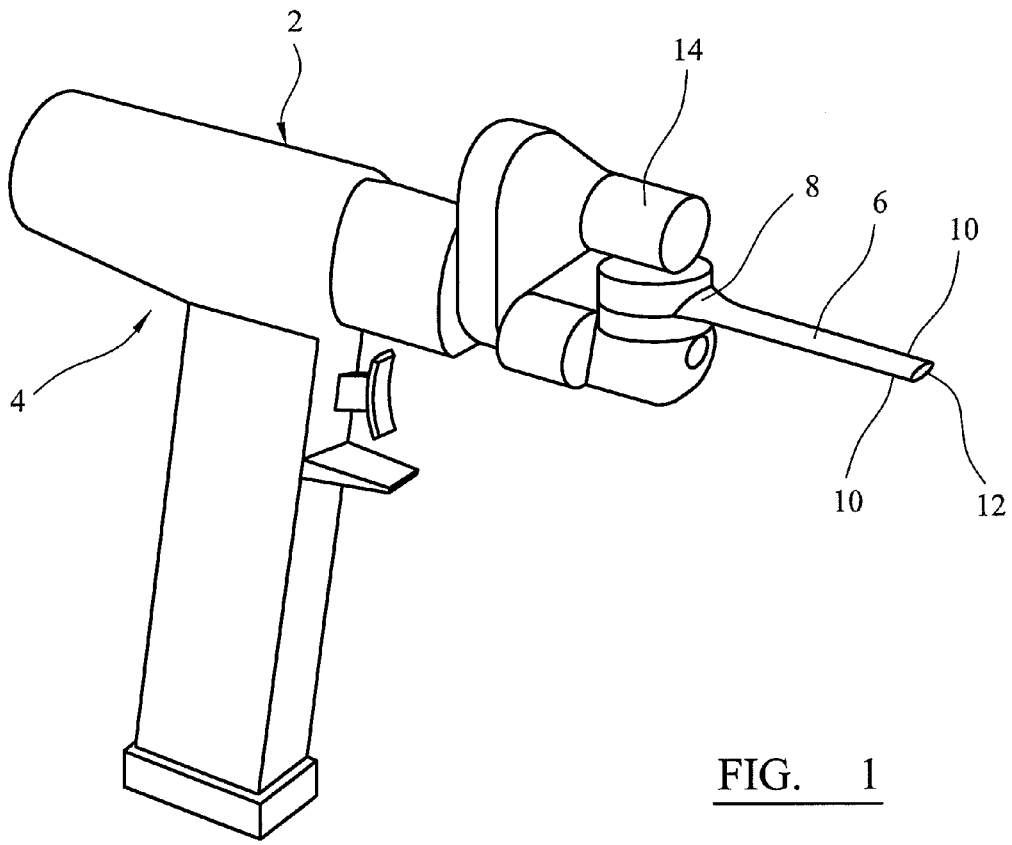
FIG. 1 is an isometric view of a reciprocating bone saw, having a light source fastened to it.

Referring to the drawings, FIG. 1 shows a powered bone saw 2 which can be used to cut a bone. It comprises a drive body 4 and a blade 6. The blade is fixed between two chuck plates 8 through which the reciprocating side-to-side motion is imparted to the blade. The blade is formed from sheet stainless steel. It is planar with two long parallel edges 10. The short edge 12 at the end of the blade which is remote from the drive body has cutting teeth formed in it. The blade is arranged in the chuck so that the plane in which it is moved by the drive contains the two parallel edges of the blade.

The bone saw has a laser unit 14 fastened to it. The laser unit generates a collimated beam of visible light in a direction which is parallel to the plane defined by the blade 6. The distance between the centre line of the blade and the centre of the beam is 20 mm.

Figure 2:
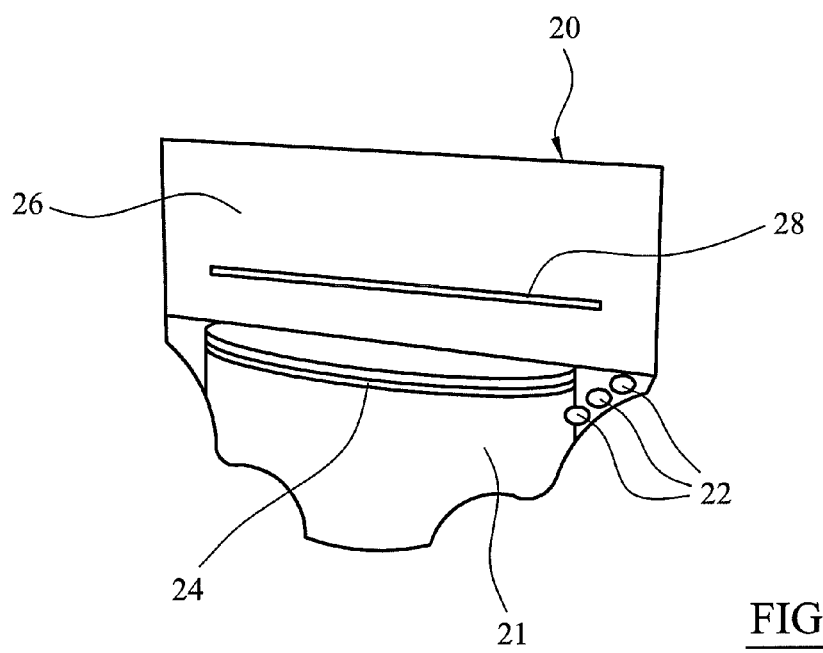
FIG. 2 is an isometric view of a cutting guide which can be used with the bone saw shown in FIG. 1.

FIG. 2 shows a cutting guide 20 which includes a body 21 formed from a block of stainless steel such as is conventionally used in the manufacture of surgical instruments. It has three fixation holes 22 at each side. It has a slot 24 formed in it in which the blade 6 of the bone saw is a sliding fit.

The cutting guide includes a screen 26 which extends upwardly from the upper face of the cutting guide body. The screen has a line 28 extending across it. The distance between the centre of the line and the centre of the saw slot 24 is 20 mm. The line is defined by a groove in the screen. The groove can contain a paint whose colour contrasts with that of the surrounding material of the screen.

Figure 3:
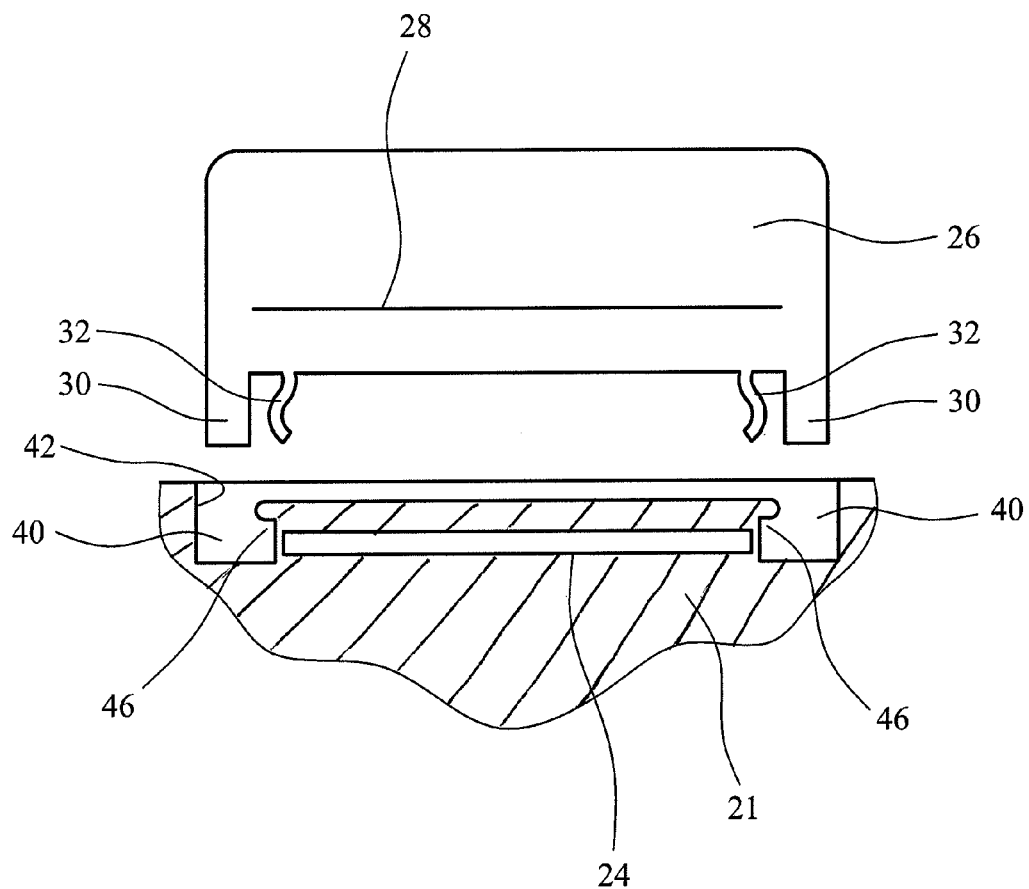
FIG. 3 is a front view partially in section of a cutting guide, together with a screen which can be fastened to the cutting guide.

FIG. 3 shows features of a screen and cutting guide body which allow the screen to be mounted detachably on the cutting guide body. The screen is made from a polypropylene by moulding. The screen has a pair of feet 30 at opposite corners. Each foot has a retaining clip 32 associated with it.

The cutting guide body has a pair of sockets 40 formed in its top face. Each of the sockets can receive one of the feet 30 on the screen with its respective retaining clip. Each of the sockets is defined by an outwardly facing end wall 42 and an inwardly facing end wall. The inwardly facing end wall defines an undercut 46. Fitting the screen on to the cutting guide body involves locating one of the feet with its respective retaining clip in the opening to one of the sockets. Application of an assembly force causes the retaining clip to be deformed until the clip can spring back into the undercut. The clip then retains the screen in position on the cutting guide body. When the screen is assembled in place on the cutting block body, the distance from the saw guide slot 24 to the line 28 on the screen is 20 mm.

The screen can be separated from the cutting guide body by application of a separating force. This force causes the retaining clips to be deformed by the inwardly facing walls of the sockets so that the feet with their respective retaining clips can be withdrawn from the sockets.

Figures 4, 5:
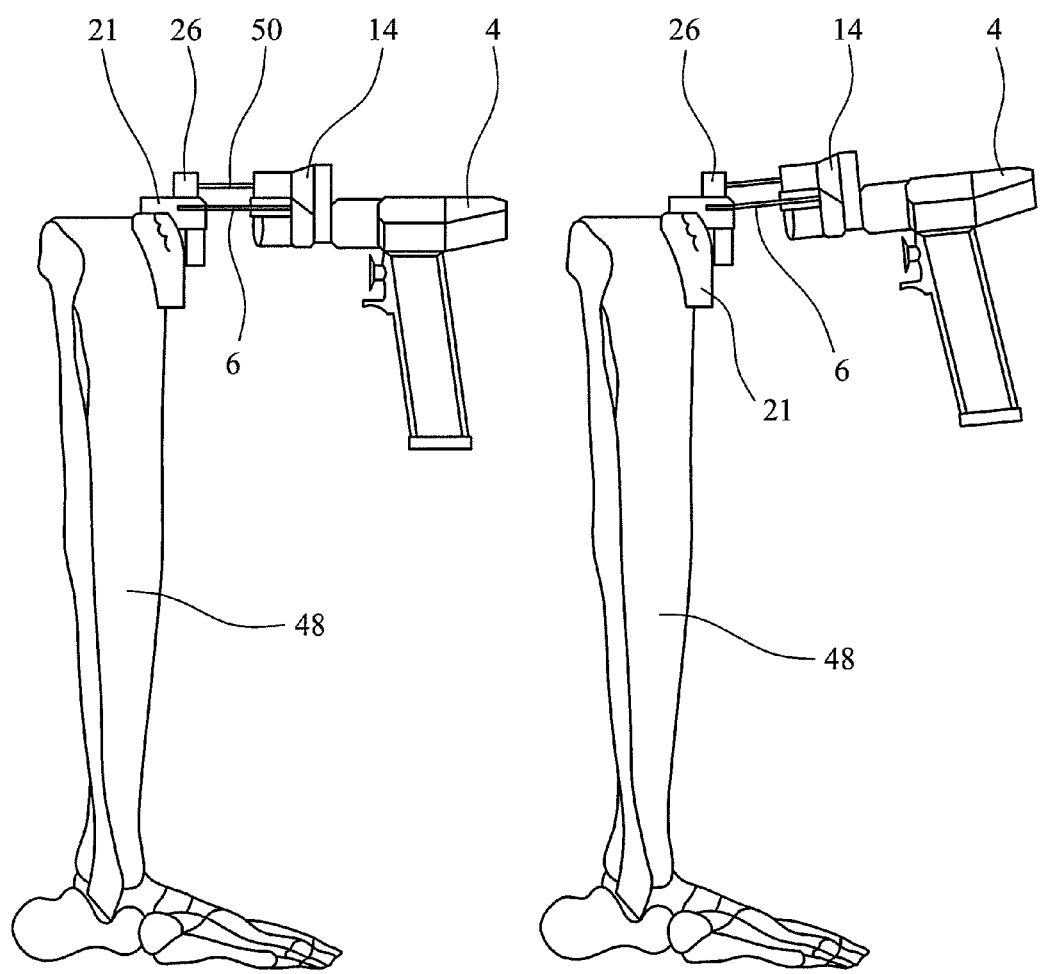
FIGS. 4 and 5 are side views of the lower leg, illustrating the use of the bone saw and cutting guide which are shown in FIGS. 1 and 2.

FIG. 4 illustrates correct alignment of the blade 6 with the slot 24 in the cutting guide. The drawing shows the cutting guide 20 fastened to the anterior face of the tibia 48, towards the proximal end thereof. It can be positioned on the tibia using alignment instrumentation as is known. The beam 50 from the laser unit 14 extends parallel to the blade and is incident on the screen 26, in the groove 28, so that movement of the saw within the slot causes the beam to move along the groove 28 but not to deviate from the groove.

If the bone saw is tipped so that the blade is no longer parallel to the plane of the saw slot in the cutting guide, as shown in FIG. 6, the light from the laser unit will not longer be coincident with the groove 28 in the screen 26. This will be apparent visibly to the surgeon who will be able to correct the orientation of the saw. Correction of the orientation of the saw will help to reduce wear of the saw blade and the cutting guide, and to reduce vibration of the cutting guide which might cause it to loosen or otherwise to move.

The drawings illustrate embodiments of the invention in which the cutting tool is a saw. The invention is applicable to other instruments such as a burr cutting tool, and a bone drill (in which the cutting guide provides a bore for the drill bit).

The invention claimed is:

1. An assembly for use in cutting a bone during a surgical procedure, comprising:
   a cutting tool having a cutter that is adapted to cut the bone along a cutter axis, the cutter being in the form of blade or of a rotatable bit, and a drive unit for imparting a cutting motion to the cutter; and
   a guide block positionable against the bone having a reference slot or bore extending along a central reference axis for guiding the cutting tool during the cutting step, the guide block having a screen surface having a reference mark thereon that indicates proper alignment of the cutter, wherein the cutting tool includes a light source positioned such that light emitted from the light source is emitted in a direction parallel to the cutter on to the screen surface when the cutter is in contact with the reference slot or bore, a distance between the cutter axis and the light beam being equal to a distance between the central reference axis and the reference mark on the screen surface.

2. The assembly of claim 1, wherein the cutter is a saw blade and the reference slot or bore is a slot that includes a reference surface that is planar, and the reference mark is a line that extends parallel to the reference surface.

3. The assembly of claim 1, wherein the cutter is a rotating bit and the reference slot or bore is a bore, and the reference mark defines a point.

4. The assembly of claim 1, wherein the light source is mounted on the cutting tool.

5. The assembly of claim 1, wherein the light source comprises a fiber optic light conduit for conveying light from a source to the cutting tool, wherein the fiber optic light conduit has a free end that is fastened to the cutting tool.

6. The assembly of claim 1, wherein the screen surface is detachably mounted on the guide block.

7. The assembly of claim 1, wherein the light source emits a collimated beam of light.

8. A method of cutting a bone, comprising the steps of:
   positioning a guide block against the bone, the guide block having a reference slot or bore extending along a central reference axis for guiding a cutter and a screen surface for providing a reference mark to indicate proper alignment of the cutter;
   positioning a cutting tool having a cutter in the form of a blade or a rotatable bit so that the cutter is positioned against the reference slot or bore, the cutting tool including a light source positioned to direct a beam of light in a direction parallel to the cutter into a position onto the screen surface when the cutter is in contact with the reference slot or bore, a distance between a cutter axis of the cutter and the beam of light being equal to a distance between the central reference axis and the reference mark on the screen surface;
   cutting the bone by activating a drive unit for imparting a cutting motion to the cutter; and
   maintaining the position of the beam of light relative to the reference mark during the cutting step.

\* \* \* \* \*